US00PP12192P2

(12) United States Plant Patent
Foley, Jr.

(10) Patent No.: US PP12,192 P2
(45) Date of Patent: Nov. 6, 2001

(54) *YUCCA RECURVIFOLIA* PLANT NAMED 'HINVARGAS'

(75) Inventor: Thomas M. Foley, Jr., Katy, TX (US)

(73) Assignee: Hines Horticulture, Inc., Irvine, CA (US)

( * ) Notice: Subject to any disclaimer, the term of this patent is extended or adjusted under 35 U.S.C. 154(b) by 0 days.

(21) Appl. No.: 09/300,578

(22) Filed: Apr. 27, 1999

(51) Int. Cl.[7] ..... A01H 5/00

(52) U.S. Cl. ..... Plt./373

(58) Field of Search ..... Plt./373

*Primary Examiner*—Bruce R. Campell
*Assistant Examiner*—June Hwu
(74) *Attorney, Agent, or Firm*—Christie, Parker & Hale, LLP

(57) ABSTRACT

A new and distinct plant variety of *Yucca recurvifolia* named 'Hinvargas' characterized by its yellow to yellow-green variegated foliage, exhibited as about 1 to 3 mm. wide vertical bands running the length of the leaves.

4 Drawing Sheets

BACKGROUND OF THE INVENTION

The present invention relates to a new and distinct variety of *Yucca recurvifolia* Salisb. Which was discovered as a whole plant mutation in a controlled planting of *Yucca recurvifolia* in Fulshear, Tex. The varietal denomination of the new variety is 'Hinvargas'.

The genus Yucca is included in the family Agavaceae which comprises about 40 genera of evergreen trees and perennial and herbaceous plants mostly originating in tropical and subtropical regions of the Northern and Southern hemispheres. The genus Yucca comprises at least 34 species of evergreen trees and perennial and herbaceous plants, many of which possess desirable ornamental characteristics. *Yucca recurvifolia* is native to the Eastern United States. It generally has lanceolate leaves to about 90 cm. long and to about 6 cm. wide. *Yucca recurvifolia* is fully evergreen depending on winter temperatures. Leaf color ranges from light to dark green, depending on light intensity and cultural conditions. Flowers of *Yucca recurvifolia* are borne on an erect, narrowly conical panicle to about 1 m. tall and about 30 cm. wide. Flowers are borne from between July to September in Texas. *Yucca recurvifolia* is believed to have been in cultivation in Europe and North America for about 200 years. Only four cultivars with colored foliage are known to have been grown: (1) *Yucca recurvifolia forma marginata* (Carr.) Trel., which has leaves with pencil-width marginal variegation; (2) *Yucca recurvifolia forma variegata* (Carr.) Trel., with central yellow variegation; (3) *Yucca recurvifolia forma elegans* Trel., which has reddish central variegation; and (4) *Yucca recurvifolia forma rufocincta* Baker, Gard., a lower-growing form with reddish-brown margins.

SUMMARY OF THE INVENTION

The new variety was discovered as a whole plant mutation in a controlled planting of *Yucca recurvifolia* in Fulshear, Tex., and differs from other known varieties of *Yucca recurvifolia* in its yellow to yellow-green variegated foliage, exhibited as between 1 to 3 mm. Wide vertical bands running the length of the leaves. Asexual reproduction of the new variety by root division performed in Irvine, Calif., Vacaville, Calif; and Fulshear, Tex., have confirmed that the distinctive characteristics of the new variety are stable and transmitted to succeeding generations, and the new variety reproduces true to type.

COMPARISON WITH PARENT

'Hinvargas' is distinguished from its parent and all other varieties of *Yucca recurvifolia* of which I am aware by its yellow to yellow-green variegated foliage, exhibited as between 1 to 3 mm. wide vertical bands running the length of the leaves.

DESCRIPTION OF ILLUSTRATIONS

The accompanying photographic illustrations show a specimen of the new cultivar as true to color as is reasonably possible to make in an illustration of this character. Specimens photographed are approximately 5 years old and were grown out of doors in Fulshear, Tex.

DETAILED DESCRIPTION OF THE NEW VARIETY

Figure 1:
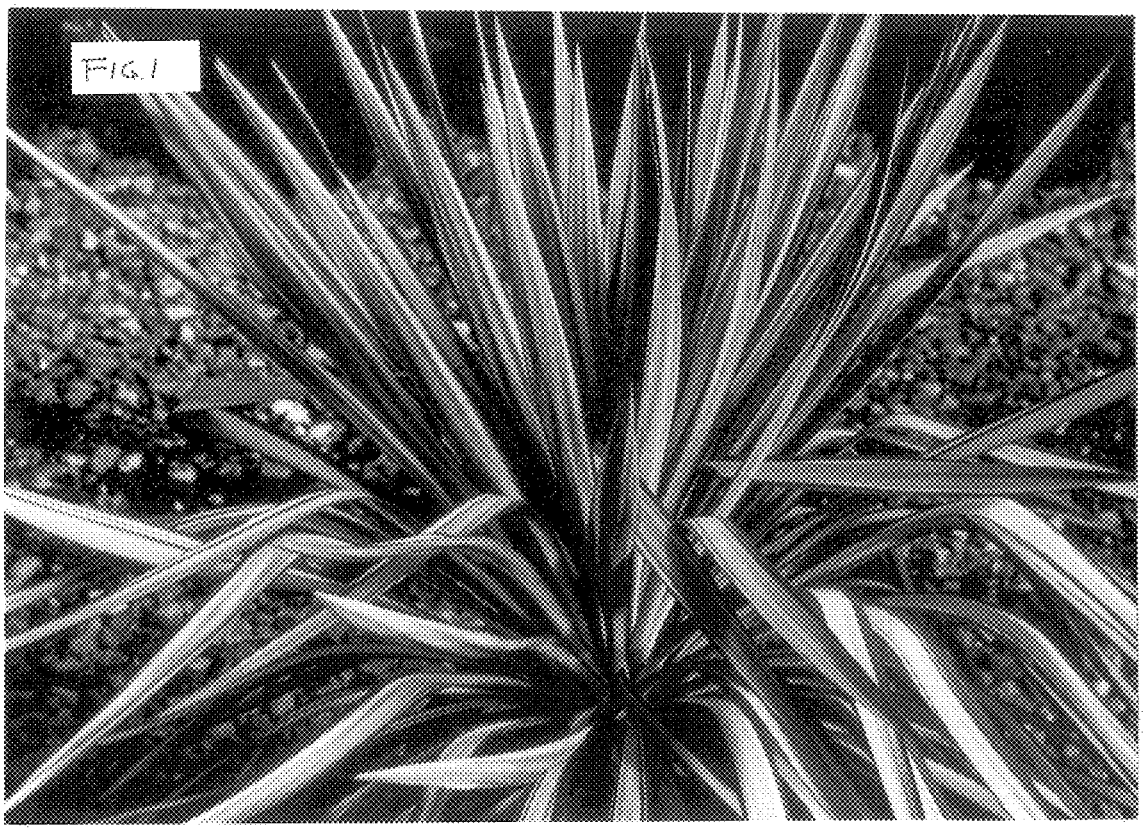
FIG 1 illustrates the distinctive foliage variegation of a mature specimen of the new variety.
Figure 2:
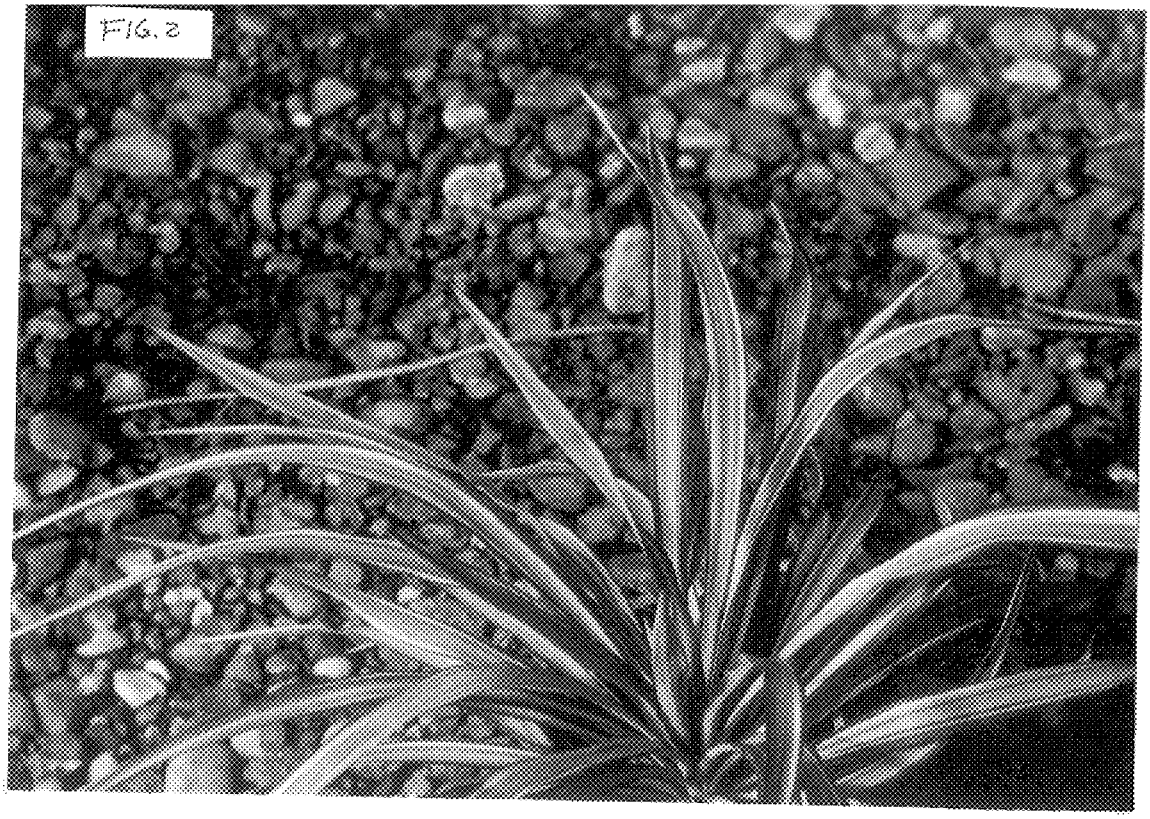
FIG 2 illustrates the distinctive foliage variegation of a mature specimen of the new variety.
Figure 3:
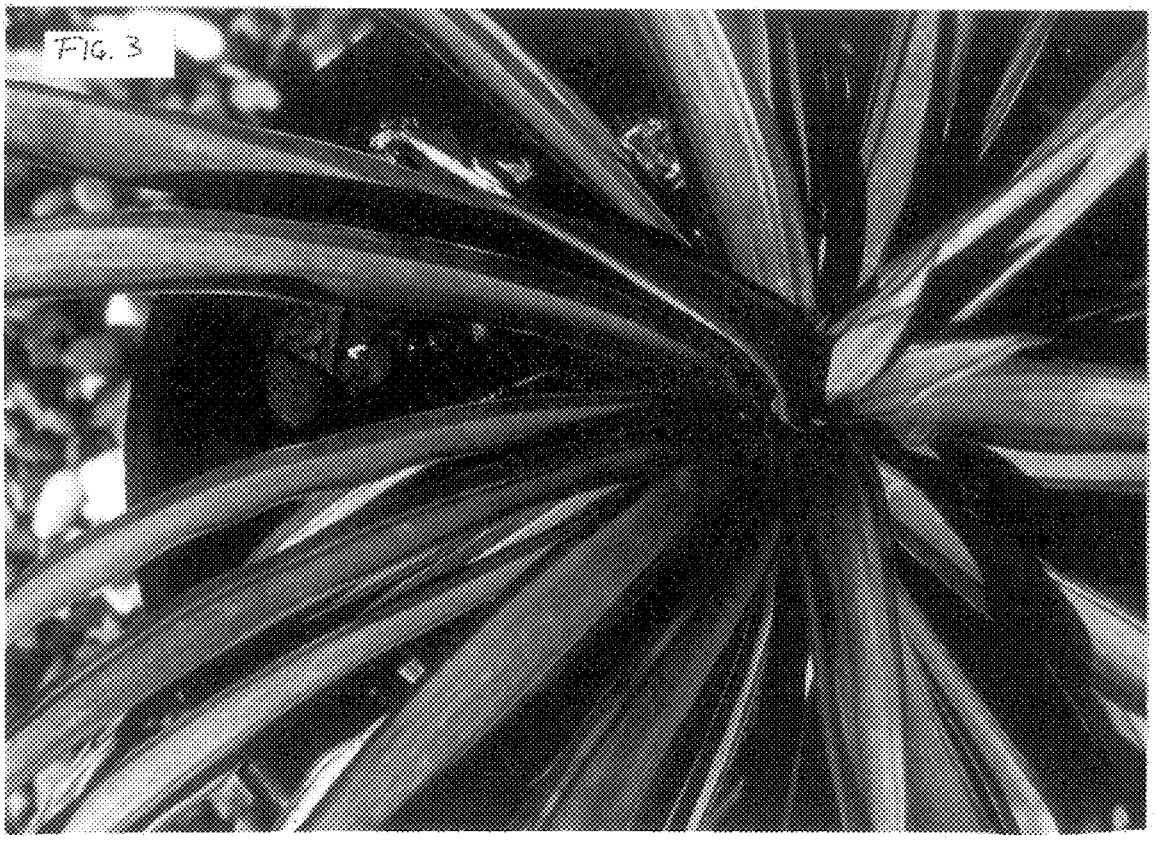
FIG 3 illustrates the maroon-colored foliage of the new variety in winter months.
Figure 4:
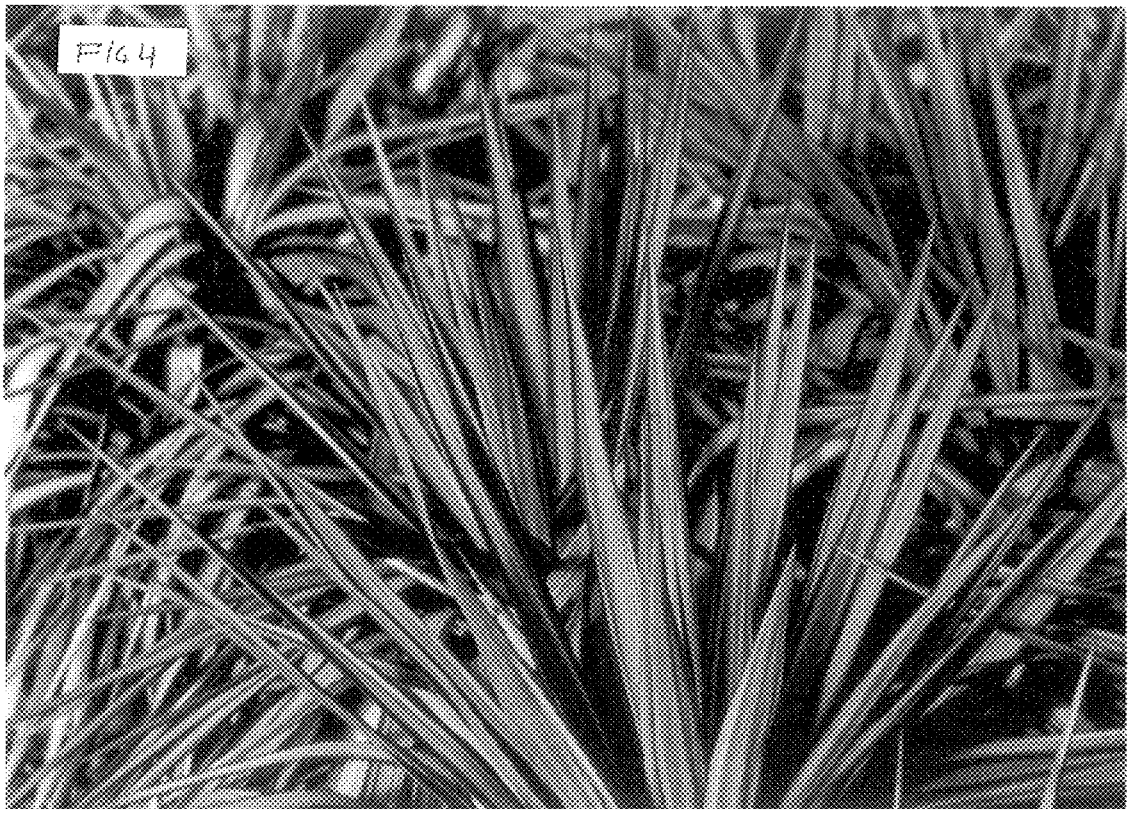
FIG. 4 illustrates the distinctive foliage variegation of a mature specimen of the new variety.

'Hinvargas' has not been observed under all possible environmental, cultural and light conditions. The following observations and descriptions are of plants grown in containers at Vacaville, Calif., Fulshear, Tex. Katy, Tex; and Apex, N.C.

In this description, color references are to The *Royal Horticultural Society Colour Chart* (1995 ) and terminology used in the color descriptions herein refers to plate numbers int his color chart. Phenotypic expression may vary with light intensity, cultural and environmental conditions.

Classification:

*Botanical.*—*Yucca recurvifolia* Salisb. 'Hinvargas'.

*Parentage.*—Root sport of the variety *Yucca recurvifolia.*

*Progagation.*—By root division.

Plant:

*Size.*—About 1.5 m. tall and about 1.0 m. wide at maturity.

*Habit.*—Upright habit with pendant leaves.

*Branching.*—Unbranched.

*Leaf.*—Arrangement: Alternate in a dense cluster or rosette. Leaf Shape: Lanceolate, closely alternate, recurved, surface nearly level. Leaf Base: Decurrent. Size: About 48 cm. long and from about 5 to 6 cm. wide. Leaf Margin: Slightly serrated; microscopic teeth. Leaf texture/substance: Pliable, with ripples present along the leaf surface; leaf surface has sandpaper-like texture.

The following Color Readings are of mature specimens (about 5 years old) grown out-of-doors, in Fulshear, Tex., April 2001.

Leaf color:

*Young leaves upper side.*—Leaf edge near Green Group 137C to 137D; variegation near Yellow Group 10C to 10D.

*Under side.*—Leaf edge near Green Group 148C to 148D; variegation near Yellow Group 10C to 10D.

*Mature leaves.*—Color varies with intensity of sunlight, cultural conditions and time of year. In winter, plants can exhibit reddish foliage (less than 10% of observed specimens exhibit this winter coloration). Striped variegation varies from about 1 mm. to 30 mm. wide.

*Upper side.*—Leaf edge near Green Group 137C to 137D; variegation near Yellow Group 10C to 10D.

*Under side.*—Leaf edge near Yellow-Green Group 148C to 148D; variegation near Yellow Group 9D.

The following Color Readings are of mature specimens (5 year old plants) grown out-of doors, in Fulshear, Tex., February 2001.

Plants exhibiting winter coloration

Upper side: Near Green Group, 137A to 137C; central variegation near Red Group 47B to 47C at and near leaf base to Red Group 52B to 52C from mid-leaf to tip.

Under side: Leaf edge near Yellow-Green Group 148C to 148D; central variegation near Yellow Group 9D.

Plants not exhibiting winter coloration

Upper side: Near Green Group, 137A to 137C at leaf center; near Green Group 138A to 138C near margin; variegation near Yellow Group 12B.

Under side: Leaf edge near Green Group 148C to 148D; variegation near Yellow Group 9D.

Venation:

*Pattern.*—Upper Surface: Parallel. Under Surface: Parallel.

*Petioles.*—None present.

*Internodes.*—Leaves are alternate along the trunk and form a whorl.

*Hardiness.*—USDA Zone 8 (20° F. to 10° F.); AHS Heat Zone 8.

*Vigor.*—*'Hinvargas'* produces 2 significant growth flushes per year, Spring and late Summer.

*Pests/diseases.*—No susceptibility to diseases/pests noted; no resistance to diseases/pests noted beyond resistance typical of the species.

Infloresence:

*Bloom period.*—Spring and late Summer (field production).

*Flower form.*—Narrowly conical panicle elevated slightly over the leaves on a scape-like stem.

*Flower arrangement.*—Perianth 6-parted; calyx of 3 sepals; corrola of 3 similar petals; style stout; ovules numerous in the cavity of each carpel.

*Flower size.*—Approximately 7.5 cm. long.

*Sepals.*—Size: About 5.5 cm. by 2.5 cm. Shape: Elliptical with acuminate apex. Color: Near White Group 155A to 155C. Texture: Smooth with prominent midrib.

*Fragrance.*—None noted.

*Lastingness of individual blooms.*—Individual flowers last for about 2 to 3 days; panicle lasts for about 3 to 4 weeks.

*Reproductive organs:*

*Stamens.*—6 shorter than the perianth, filaments enlarged above, anthers sagittate.

*Gynoecium.*—Syncarpous.

*Style.*—Stout.

*Carpels.*—About 3.

*Ovules.*—Numerous (between 21 to 36) in the cavity of each carpel.

*Stigma.*—Bipartite.

*Anthers.*—Saggittate.

*Pistils.*—Typical number is about 3; number observed is 3.

*Pollen.*—Typical Amount Produced: Each anther produces a small amount of pollen. Observed Amount Produced: Small tufts of grains. Color: Near Yellow Group 4C to 4D.

*Fruit.*—Type: Loculicidal capsule. Observed amount: No capsules observed to date.

I claim:

1. A new plant of *Yucca recurvifolia* of the variety substantially as shown and described.

* * * * *